United States Patent
Fang et al.

(10) Patent No.: US 7,087,811 B1
(45) Date of Patent: Aug. 8, 2006

(54) ENHANCED PROTEIN PRODUCTION IN HIGHER PLANTS BY N-TERMINAL FUSION OF A UBIQUITIN OR A CUCUMBER MOSAIC VIRUS COAT PROTEIN PEPTIDE

(75) Inventors: Rong-Xiang Fang, Beijing (CN); Jun-Lin Wu, McLean, VA (US); Xiao-Ying Chen, Beijing (CN)

(73) Assignee: Agency for Science, Technology and Research, Centros (SG)

( * ) Notice: Subject to any disclaimer, the term of this patent is extended or adjusted under 35 U.S.C. 154(b) by 0 days.

(21) Appl. No.: 09/857,841

(22) PCT Filed: Dec. 11, 1998

(86) PCT No.: PCT/SG98/00103

§ 371 (c)(1),
(2), (4) Date: Aug. 30, 2001

(87) PCT Pub. No.: WO00/36129

PCT Pub. Date: Jun. 22, 2000

(51) Int. Cl.
*C12N 15/82* (2006.01)
*C12N 15/40* (2006.01)
*C12N 15/62* (2006.01)
*C12N 5/04* (2006.01)
*A01H 5/00* (2006.01)

(52) U.S. Cl. ............... 800/288; 800/278; 435/69.7; 435/320.1; 435/419; 435/468; 536/23.4; 536/23.72

(58) Field of Classification Search ............... 435/69.1, 435/69.7; 536/23.6, 23.1; 800/278, 288, 800/298
See application file for complete search history.

(56) References Cited

U.S. PATENT DOCUMENTS 5,773,705 A  6/1998  Vierstra et al.

FOREIGN PATENT DOCUMENTS

| EP | 0 672 754 A1 | 9/1995 |
|---|---|---|
| WO | WO 90/02189 A1 | 3/1990 |
| WO | WO 96/03519 A1 | 2/1996 |
| WO | WO 96/03522 A1 | 2/1996 |
| WO | WO 96/21018 A1 | 7/1996 |

OTHER PUBLICATIONS

Ecker et al., J. Biol. Chemistry. 1989, vol. 264, No. 13, pp. 7715-7719.*
Garbarino et al., "Isolation of a ubiquitin-ribosomal protein gene (ubi3) from potato and expression of its promoter in transgenic plants," Plant Molecular Biology 24:119-127, 1994.
Garbarino et al., "Isolation of a Polyubiquitin Promoter and Its Expression in Transgenic Potato Plants," Plant Physiol. 109:1371-1378, 1995.
Genschik et al., "Structure and promoter activity of a stress and developmentally regulated polyubiquitin-encoding gene of *Nicotiana tabacum*," Gene 148:195-202, 1994.
Haq et al., "Biological, serological and molecular characterization of a cucumber mosaic virus isolate from India," Plant Pathol. 45:823-828, 1996.
Karrer et al., "Cloning of tobacco genes that elicit the hypersensitive response," Plant Mol. Biol. 36:681-690, 1998.
GenBank Accession No. X89652 (Mar. 25, 1997).
GenPept Accession No. AAC49970 (Mar. 18, 1998).

* cited by examiner

*Primary Examiner*—David T. Fox
(74) *Attorney, Agent, or Firm*—Rothwell Figg Ernst & Manbeck

(57) ABSTRACT

Methods are disclosed for enhancing protein production. One method comprises preparing a vector by inserting a gene encoding ubiquitin in front of a gene encoding a protein of interest and inserting the vector into a cell. A fusion protein will be expressed which includes ubiquitin plus the protein of interest. Ubiquitin C-terminal hydrolases can cleave the fusion protein leaving the desired protein in its free state. This method causes enhanced production of the protein of interest as compared to performing the same method without the ubiquitin gene as part of the vector. A ubiquitin promoter is unnecessary to yield this enhanced production and is not used. A second method is very similar except that in place of a ubiquitin gene, a gene encoding fourteen amino acids of cucumber mosaic virus coat protein is inserted in front of the gene of interest. This results in expression of a fusion protein comprising the fourteen amino acid residues of the coat protein bonded to the protein of interest. The fusion protein is produced at a higher level than is the protein when the coat protein gene fragment is not present in the vector. In both methods the genes can be placed under the control of heterologous promoters such as a 35S promoter.

15 Claims, 11 Drawing Sheets

SphI

```
  GC ATG CAG ATC TTC GTA AAG ACC CTG ACG GGG
   1  M   Q   I   F   V   K   T   L   T   G
     AAG ACT ATT ACC TTA GAG GTA GAG TCA TCG
  11  K   T   I   T   L   E   V   E   S   S
     GAC ACC ATT GAC AAT GTT AAG GCT AAG ATT
  21  D   T   I   D   N   V   K   A   K   I
     CAG GAC AAG GAA GGC ATT CCA CCG GAC CAG
  31  Q   D   K   E   G   I   P   P   D   Q
     CAG CGG TTG ATT TTC GCA GGT AAG CAG CTT
  41  Q   R   L   I   F   A   G   K   Q   L
     GAG GAT GGC CGA ACA CTA GCT GAC TAC AAC
  51  E   D   G   R   T   L   A   D   Y   N
     ATC CAG AAG GAG TCC ACT CTC CAT CTC GTC
  61  I   Q   K   E   S   T   L   H   L   V
     TTA AGA CTC CGC GGT GGC CATGG
  71  L   R   L   R   G   G
                                    NcoI
```

FIG. 1

```
BamHI
     1   M    D    K    S    E    S    T    S
  GATCCATG  GAC  AAA  TCT  GAA  TCA  ACC  AGT
            TAC  CTG  TTT  AGA  CTT  AGT  TGG  TCA

A    G    R    N    R    R    14
 GCT  GGT  CGT  AAC  CGT  CGA  CGAGCT
 CGA  CCA  GCA  TTG  GCA  GCT  GC
                          AccI      SstI
```

FIG. 2

ENHANCED PROTEIN PRODUCTION IN HIGHER PLANTS BY N-TERMINAL FUSION OF A UBIQUITIN OR A CUCUMBER MOSAIC VIRUS COAT PROTEIN PEPTIDE

BACKGROUND OF THE INVENTION

Strategies for production of proteins in heterologous fusion form have been widely applied in biotechnology for many purposes, such as secretion of proteins from host cells (fused to signal peptides), easy detection or purification of protein products (fused to reporter enzymes for detection and to peptide tags for purification), searching for proteins with desired biological activities (e.g., in the phage display technique and the two-hybrid system). Enhanced expression of proteins of interest has also been achieved by N-terminal fusion of a small peptide to the target protein. Fusion of a ubiquitin gene together with a ubiquitin promoter to the 5'-end of a gene of interest is one of the systems which has been used to enhance protein expression. Ubiquitin exists in all eukaryotic cells and is the most highly conserved protein yet identified. It is abundant in cells and exhibits profound stability to heat and proteolytic degradation. Moreover, ubiquitin precursors, that is, polyubiquitin where ubiquitin monomers are linked up head to tail and ubiquitin extension proteins where a single ubiquitin is appended at its C-terminus to either of two small ribosomal proteins, undergo rapid processing by ubiquitin C-terminal hydrolases, which cleave C-terminal of the ubiquitin moieties and release the free ubiquitin monomer and the C-terminal extension proteins. All of these features have rendered ubiquitin as an excellent N-terminal fusion partner to augment target protein accumulation in genetic engineering.

The ubiquitin fusion approach was first developed by Butt et al. (1989), who showed that fusion of ubiquitin to yeast metallothionein or to the α subunit of the adenoylate cyclase-stimulatory GTP-binding protein increased the yield of these otherwise unstable or poorly expressed proteins from undetectable levels to 20% of the total cellular proteins in $E.$ $coli$. Ecker et al. (1989) demonstrated that in yeast, ubiquitin fusion resulted in enhanced expression of three mammalian proteins by up to 200-fold and all these ubiquitin fusion proteins were correctly processed by yeast ubiquitin-specific endopeptidase to release authentic functional proteins. A similar yeast ubiquitin fusion expression system was reported by Sabin et al. (1989), in which ubiquitin/human γ-interferon and ubiquitin/α1-proteinase inhibitor were highly expressed and quantitatively cleaved to yield γ-IFN and α1-PI with authentic amino termini.

Since these early reports, a wealth of studies on ubiquitin fusion expression of various proteins in $E.$ $coli$ and yeast have been described (Baker et al., 1994; Barr et al., 1991; Coggan et al., 1995; Gali and Board, 1995; Gehring et al., 1995; Han et al., 1994; Kiefer et al., 1992; Lu et al., 1990; Lyttle et al., 1992; Mak et al., 1989; McDonnell et al., 1989; McDonnell et al., 1991; Pilon et al., 1996; Poletti et al., 1992; Rian et al., 1993; Tan and Board, 1996; Welch et al., 1995). Very often fusion to ubiquitin led to dramatic enhancement in yield of the fusion protein in bacteria, or of the cleaved product in yeast.

Enhanced expression of foreign proteins by ubiquitin fusion has also been observed in plants. In analysis of the promoter of the tobacco polyubiquitin gene, Ubi.U4, by driving transient expression of the GUS reporter in tobacco protoplasts, Genschik et al. (1994) found deletion of the intron sequence from the Ubi.U4 fragment spanning from −263 to the end of the first ubiquitin-coding unit had no detectable influence on the GUS activity, but further deletion of the ubiquitin-coding sequence diminished the GUS activity by 55%.

None of these studies has shown the direct enhancing function of the ubiquitin fusion from a heterologous promoter. Garbarino and Belknap (1994) observed that fusion of the promoter plus ubiquitin-coding region of the potato ubiquitin extension protein gene ubi 3 to the GUS reporter gene resulted in GUS activity 5- to 10-fold higher than the direct fusion of the ubi 3 promoter to the GUS gene did in transgenic potato. Again, the synergistic effect of the ubi 3 promoter and the ubiquitin-coding sequence on the enhanced GUS activity was not excluded. In another study with a potato polyubiquitin gene, ubi 7, the same group (Garbarino et al., 1995) demonstrated that in transgenic potato plants GUS expression level from the fusion construct containing the ubi 7 promoter-5' untranslated sequence-intron-first ubiquitin coding unit was 10 times higher than that derived by only the ubi 7 promoter with the 5' untranslated sequence. However, the effects of the intron and the ubiquitin protein fusion in increasing expression level of the GUS reporter were not clearly discriminated.

In addition to the above mentioned journal papers, a number of patents related to the ubiquitin fusion technology have been filed since 1989. They are shown in Table 1. The publications and other materials used herein to illuminate the background of the invention or provide additional details respecting the practice, are incorporated by reference, and for convenience are respectively grouped in the appended List of References.

TABLE 1

Patents related to the ubiquitin fusion technology

| Title | Inventor | Pat. No. | Filing Date | Host cells |
|---|---|---|---|---|
| Generating desired amino-terminal residue in protein | MIT | WO 8909829 | Oct. 19, 1989 | |
| Regulation metabolic stability of a protein | MIT | US 5093242 | Mar. 3, 1992 | mammal, yeast |
| Nucleic acid constructs, malaria polypeptides and vaccines | Chiron | WO 9208795 | May 29, 1992 | yeast |
| Production of a protein with a predetermined amino-terminal amino acid residue | MIT | US 5196321 | Mar. 23, 1993 | $E.$ $coli$ |
| Yeast expression system for retinoid-X receptor | American Cyanamid | EP 608532 | Aug. 3, 1994 | yeast |
| Recombinant DNA vectors | Mascarenhas | WO 9423040 | Oct. 13, 1994 | $E.$ $coli$ |

TABLE 1-continued

Patents related to the ubiquitin fusion technology

| Title | Inventor | Pat. No. | Filing Date | Host cells |
|---|---|---|---|---|
| New heat-inducible N-degron protein and nucleic acid encoding it | Varshavsky, Dohmen, Johnston, Wu | WO 9521269 | Aug. 10, 1995 | |
| Fusion proteins containing the N-or C-terminal of ubiquitin | Varshavsky, Johnston | WO 9529195 | Nov. 2, 1995 | |
| New fusion protein of ubiquitin plant and lytic peptide | Carbarino, Jaynes, Belknap | WO 9603519 | Feb. 8, 1996 | plant |
| Production of tissue factor pathway-inhibitor in yeast cells | Innis, Creasey | WO 9604377 | Feb. 15, 1996 | yeast |
| Stable recombinant ubiquitin-lytic peptide fusion protein | J. Jaynes | WO 9603522 | Feb. 8, 1996 | plant |
| Fusion protein encoded by a gene construct | Bachmair, Finley, Varshavsky | US 5496721 | May 3, 1990 | mammal, yeast |

SUMMARY OF THE INVENTION

In accordance with the present invention a method for enhancing expression of proteins in plants or plant cells is achieved by the fusion of a ubiquitin monomer coding sequence to the 5' end of the coding sequence of the proteins. Expression of the ubiquitin fusion proteins is driven by a promoter other than promoters from polyubiquitin protein genes or ubiquitin extension protein genes. Thus enhancement of expression level of the proteins is due to the 5' terminal addition of the ubiquitin monomer coding sequence. The ubiquitin fusion proteins are cleaved at the carboxy-terminal glycine 76 residue of the ubiquitin, presumably by plant ubiquitin specific proteases, to produce proteins with desired biological properties. A second aspect of this invention is that the N-terminal peptide of 14 amino acid residues of cucumber mosaic virus coat protein (NP14) can be used as an N-terminal fusion partner to increase the expression level of target proteins in plants. The N-terminal fusion approaches described in this invention allow higher yield production of proteins in plants, either in the authentic forms in the ubiquitin fusion system or as the fusion protein in the NP14 fusion system.

BRIEF DESCRIPTION OF THE FIGURES

FIG. 1 shows the nucleotide sequence and deduced amino acid sequence of tobacco ubi.NC89. The nucleotide sequence is listed as SEQ ID NO:1 and the amino acid sequence is SEQ ID NO:2 in the Sequence Listing. The primers used in PCR are underlined and the mended 37-mer oligonucleotide is double-underlined.

FIG. 2 shows the synthetic DNA coding for the 14 N-terminal amino acids of CMV CP (NP14). The nucleotide sequence is SEQ ID NO:3 and the amino acid sequence is SEQ ID NO:4.

DETAILED DESCRIPTION OF THE INVENTION

Figure 3:
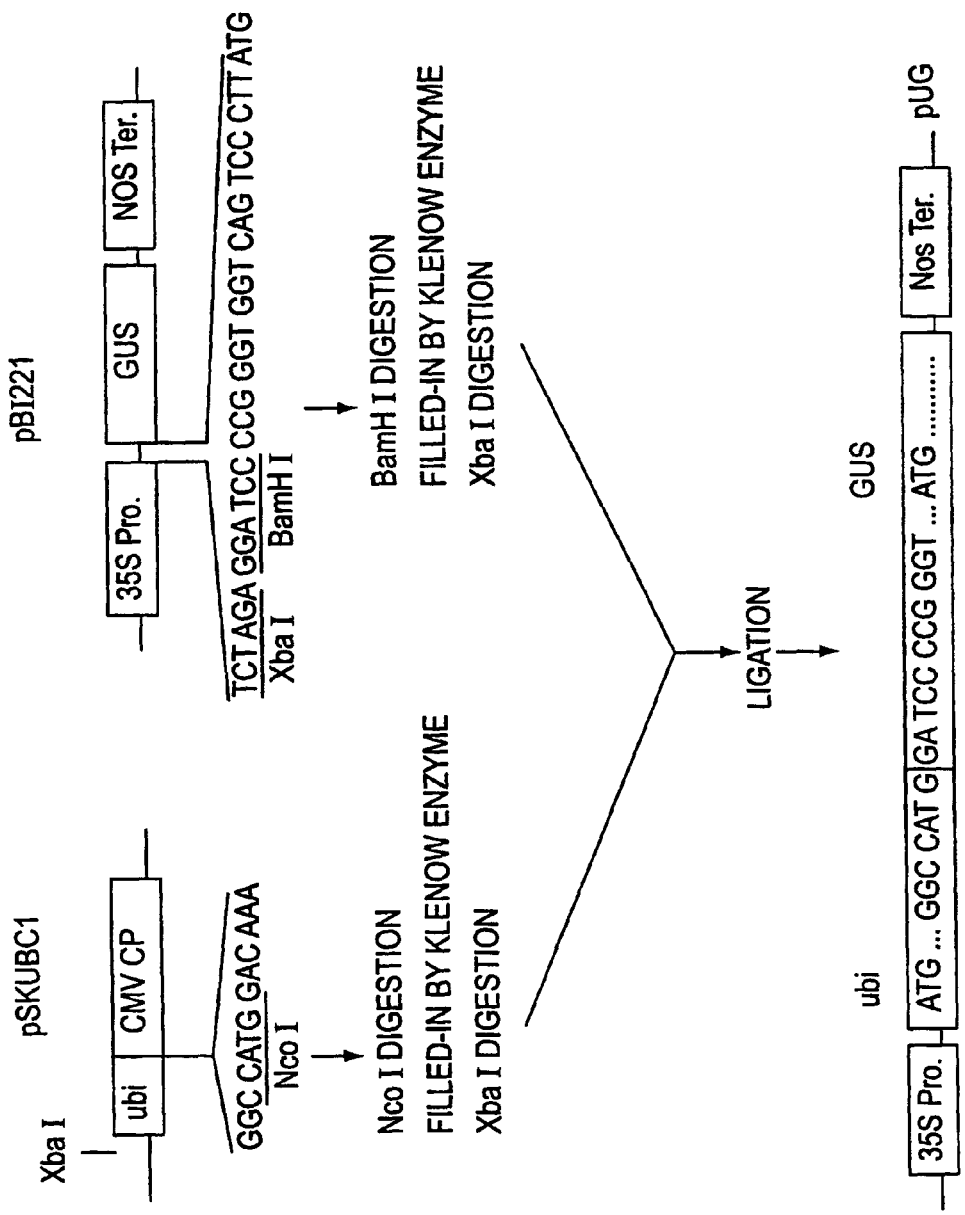
FIG. 3 illustrates the construction of the ubiquitin-GUS fusion protein expression vector pUG. The nucleotide sequence shown for pSKUBC1 is SEQ ID NO:5, the sequence shown for pBI122 is SEQ ID NO:6, and the sequence shown for pUG is SEQ ID NO:7.

The present invention is directed to methods and constructs for enhancing protein production in plants. The methods comprise fusing an expression-enhancing nucleic acid at the 5' terminus of the gene for which enhanced expression is desired. In one aspect of the invention, a ubiquitin gene is inserted in front of the gene encoding the desired protein such that a fusion protein is produced wherein ubiquitin is directly fused to the amino terminus of the desired protein. Enzymes such as C-terminal hydrolases, will cleave at the C-terminus of the ubiquitin in the fusion protein thereby releasing the desired protein in its natural form as well as forming free ubiquitin. The presence of the ubiquitin gene in the resulting fusion protein results in enhanced expression of the gene thereby yielding a greater amount of the desired protein product than occurs in the absence of the ubiquitin gene. It is necessary to use only the coding portion of the ubiquitin gene. The ubiquitin promoter is unnecessary, and the ubiquitin gene fusion can be under the control of a heterologous promoter.

In a second aspect of the invention, enhanced protein production is seen when a nucleic acid encoding 14 amino acids of cucumber mosaic virus coat protein is placed in front of the gene encoding a desired protein such that a fusion protein is produced wherein the fusion protein includes the 14 amino acids of the cucumber mosaic virus coat protein at the amino terminus of the fusion protein.

The aspects of the invention are set out in the following Examples which are offered by way of illustration and are not intended to limit the invention in any manner. Standard techniques well known in the art or the techniques specifically described below are utilized. Techniques such as transfection of protoplasts, preparation of transgenic tobacco plants, fluorometric GUS assays and luciferase assays are well known to those of skill in the art and are not described in detail herein.

EXAMPLE 1

DNA Sequences Coding for the Tobacco Ubiquitin and the N-terminal Peptide of CMV Coat Protein The coding sequence of the ubiquitin monomer contains 228 base pairs. The 5' part of 191 base pairs was obtained by polymerase chain reaction (PCR) amplification on the total DNA of Nicotiana tobacum var. NC89 and the remaining 37 base pairs were prepared as a synthetic oligonucleotide. An SphI site encompassing the initiation codon ATG and an NcoI site following the last codon GGC were created to facilitate cloning. The tobacco ubiquitin coding sequence was then cloned into pGEM-5ZF and sequenced. FIG. 1 shows the DNA sequence and the deduced amino acid sequence of the tobacco ubiquitin. The 76-amino acid sequence is identical to that derived from a tobacco polyubiquitin gene ubi.U4 (Genschik et al., 1994). However, the nucleotide sequence of the region amplified from the tobacco DNA is different from the corresponding regions of all ubiquitin monomers found in ubi.U4. We have named this tobacco ubiquitin coding sequence as ubi.NC89.

The cucumber mosaic virus coat protein (CMV CP) is encoded by the viral subgenomic RNA 4 and comprises 218 amino acid residues. The CP gene of the strain CMV-SD was cloned by RT-PCR (Guo et al., 1993) and the cDNA sequence encoding the 14 N-terminal amino acids (NP14) was either cut out of the CP gene by NcoI/AccI digestion or chemically synthesized. In the synthesized version of the NP14 coding sequence (FIG. 2), overhanging adapters for BamIII and SstI sites were attached to the 5'- and 3'-ends, respectively, for easy cloning.

EXAMPLE 2

Translational Fusion Constructs for Transient Expression Assays

A. Ubiquitin-GUS Fusion Construct pUG

The ubi.NC89 sequence was taken from the plasmid pSKUBC1 as an XbaI-NcoI (filled-in) fragment and inserted into the XbaI-BamHI (filled-in) site upstream of the GUS gene in pBI221 to construct pUG as shown in FIG. 3.

B. NP14-GUS Fusion Construct pCG

Figure 4:
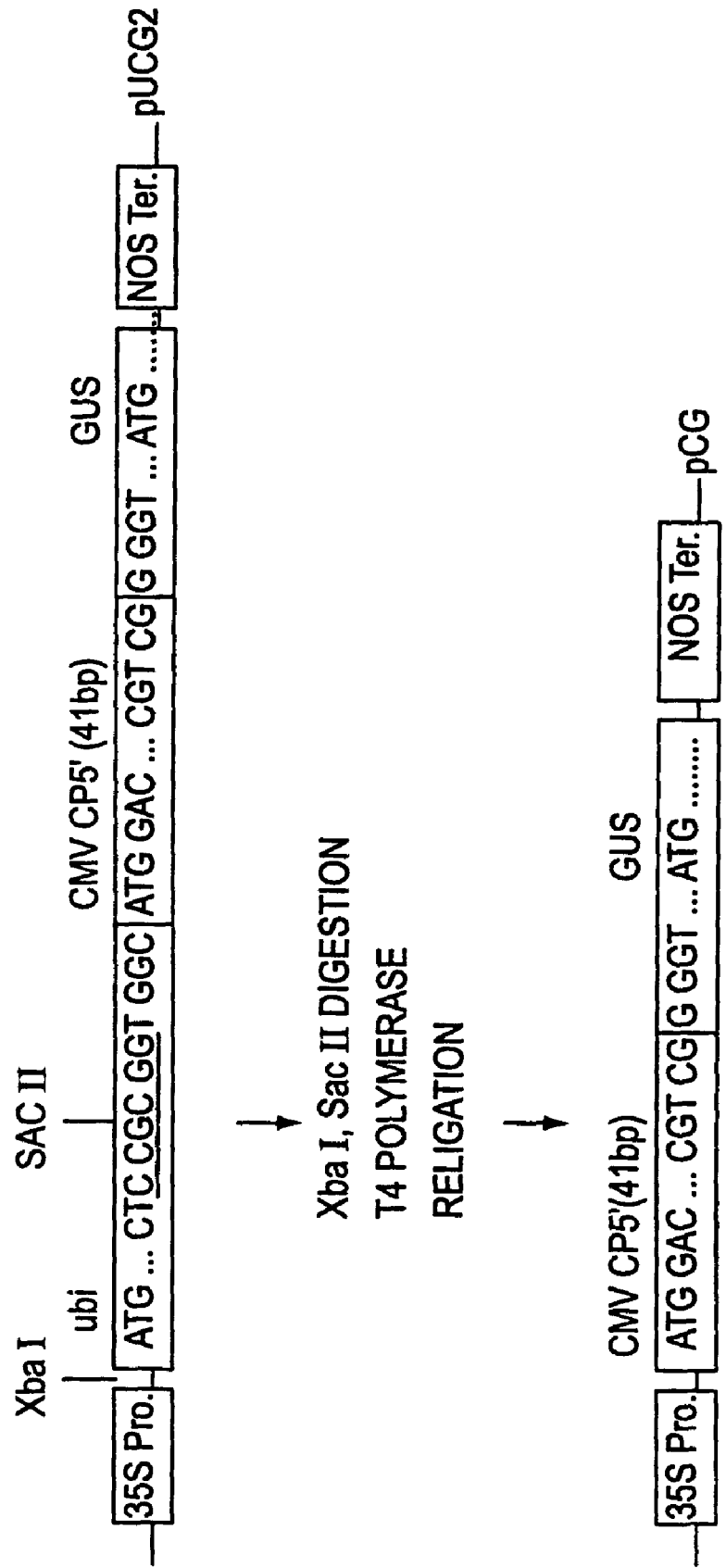
FIG. 4 illustrates the construction of the NP14-GUS fusion protein expression vector pCG. The nucleotide sequence shown for pUCG2 is SEQ ID NO:8.

Plasmid pUCG2 is a derivative of pBI221, in which the ubi.NC89 sequence and the NP14 sequence, linked as a read-through ORF, was inserted into the XbaI-SmaI sites in front of the GUS gene. The ubiquitin moiety was removed from pUCG2 by XbaI-SacII digestion and pCG was formed by recircularizing. FIG. 4 illustrates these steps clearly.

C. Ubiquitin-LUC Fusion Construct pUL

Figure 5:
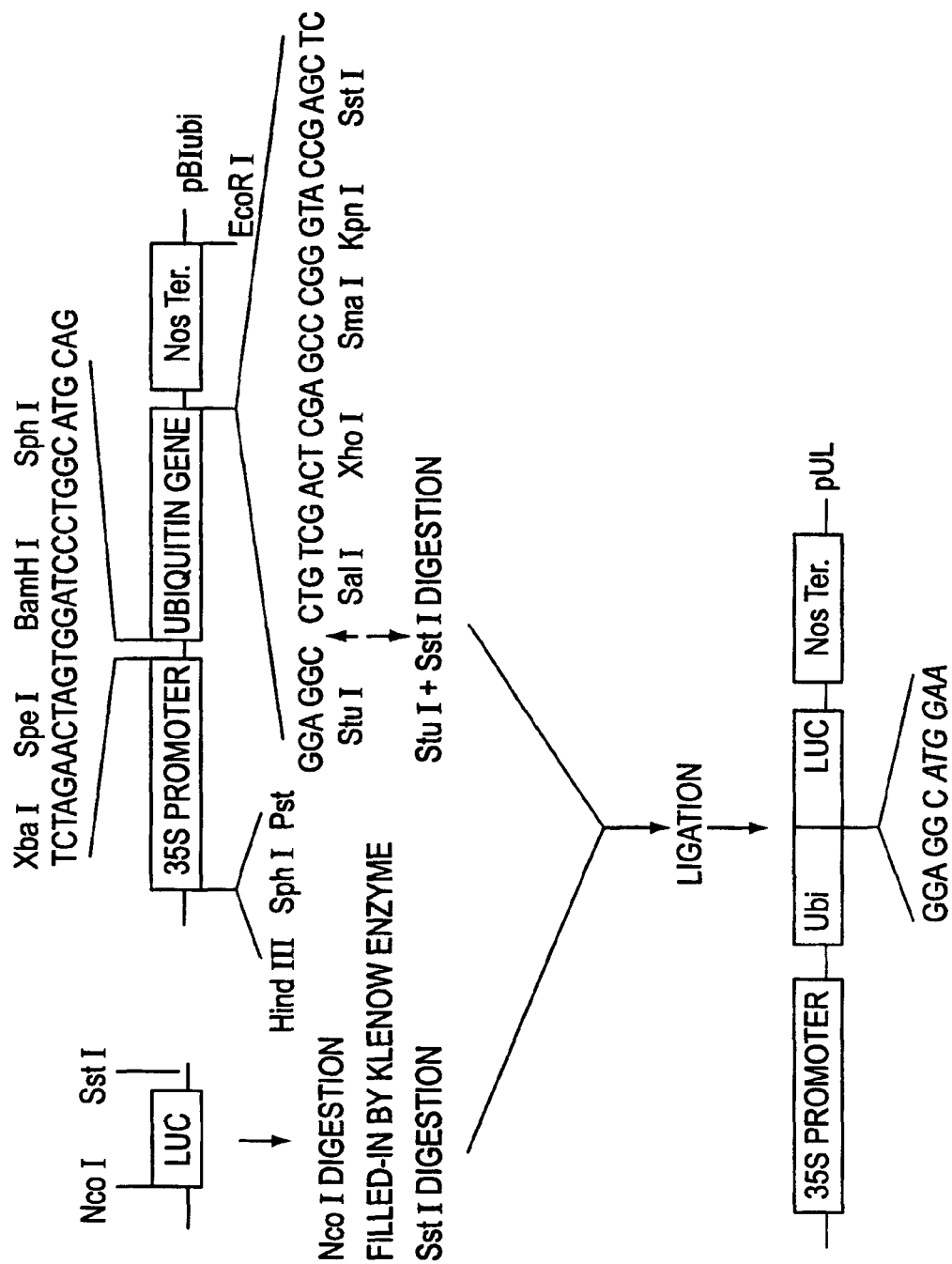
FIG. 5 illustrates the construction of the ubiquitin-luciferase fusion protein expression vector pUL. The arrow marked in the recognition sequence of Stu I in pBIubi indicates the end of the ubiquitin coding region and the cleavage site of the ubiquitin fusion protein. The upper nucleotide sequence shown for pBIubi is SEQ ID NO:9, the lower nucleotide sequence shown for pBIubi is SEQ ID NO:10, and the nucleotide sequence shown for pUL is SEQ ID NO:11.
Figure 10:
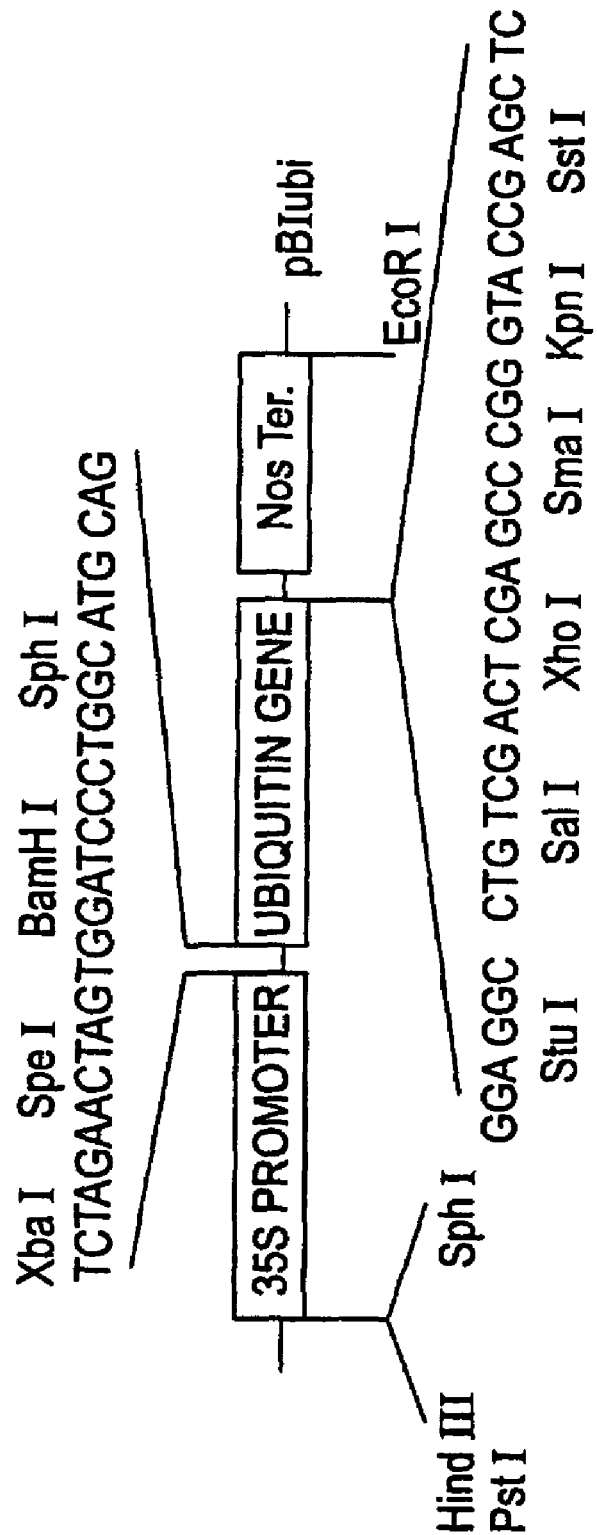
FIG. 10 illustrates the ubiquitin fusion cloning vector pBIubi. The upper nucleotide sequence is SEQ ID NO:13 and the lower nucleotide sequence is SEQ ID NO:14.

An NcoI (filled-in)-SstI fragment containing the firefly luciferase (LUC) gene was inserted into the ubiquitin fusion vector pBIubi (see FIG. 10) downstream of ubi.NC89 via the StuI-SstI sites in the polylinker region, resulting in pUL as shown in FIG. 5.

D. NP14-LUC Fusion Construct pCL

Figure 6:
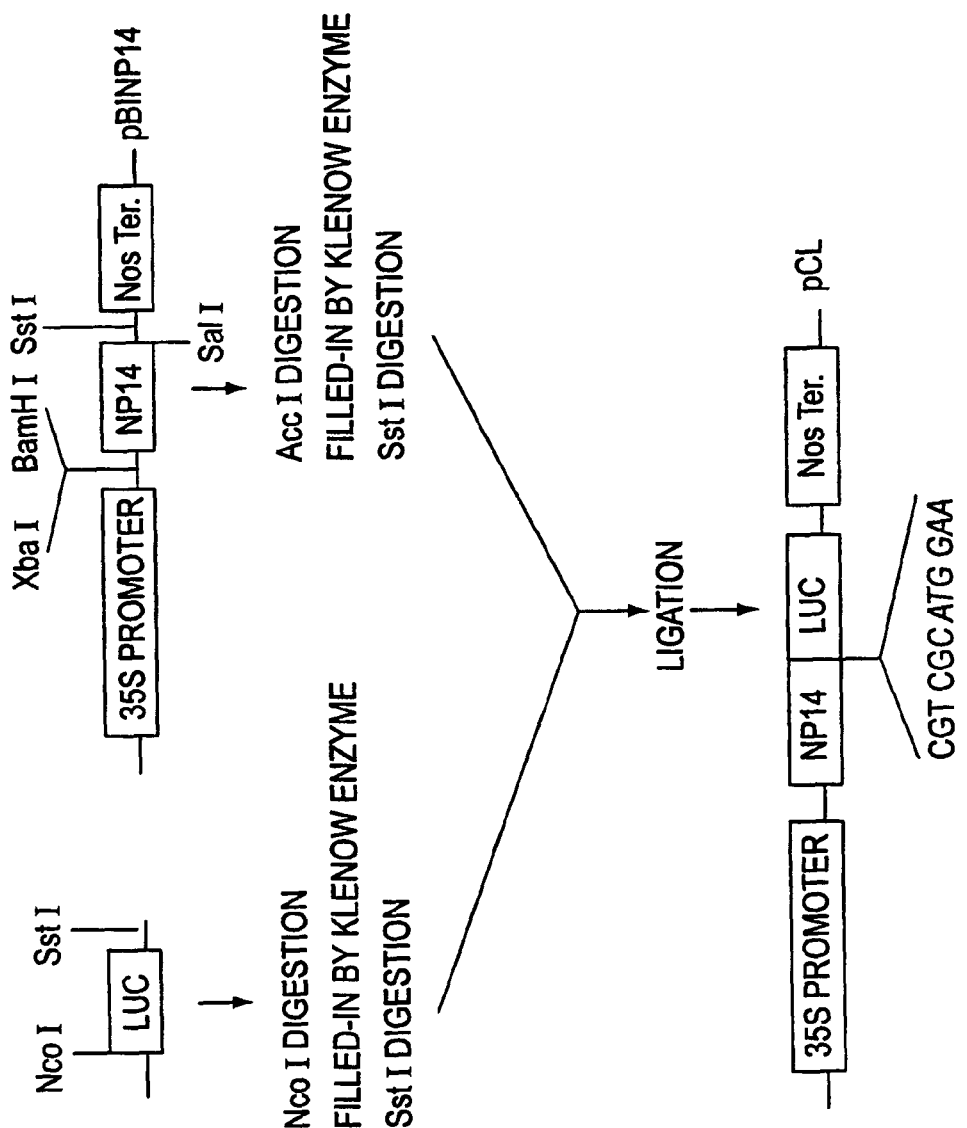
FIG. 6 illustrates the construction of the NP14-luciferase fusion protein expression vector. The nucleotide sequence shown for pCL is SEQ ID NO:12.
Figure 11:
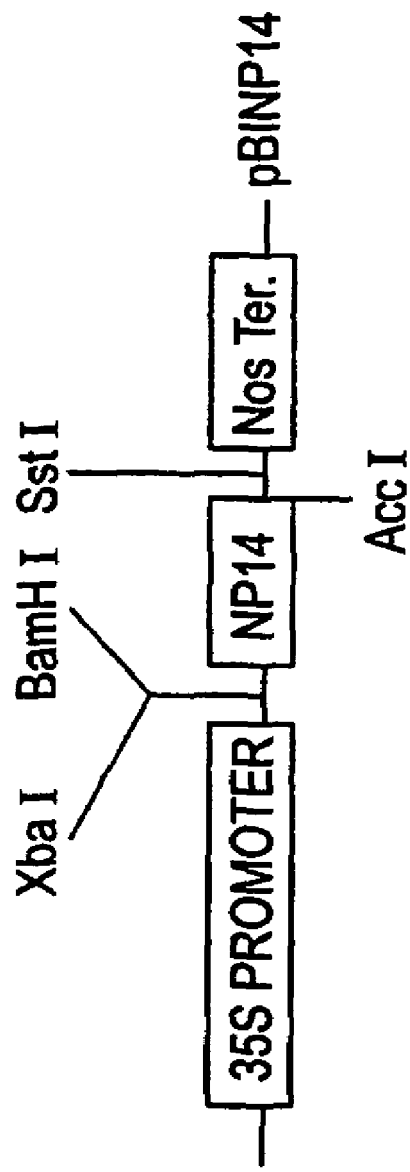
FIG. 11 illustrates the NP14 fusion cloning vector pBINP14.

The NcoI (filled-in)-SstI fragment containing the LUC gene was inserted into the NP14 fusion vector pBINP14 (see FIG. 11) downstream of the NP14 coding sequence via AccI (or SalI which is the equivalent site here) (filled-in)-SstI sites, resulting in pCL as shown in FIG. 6.

EXAMPLE 3

GUS/LUC Dual Reporter Constructs for Stable Transformation

Figure 7:
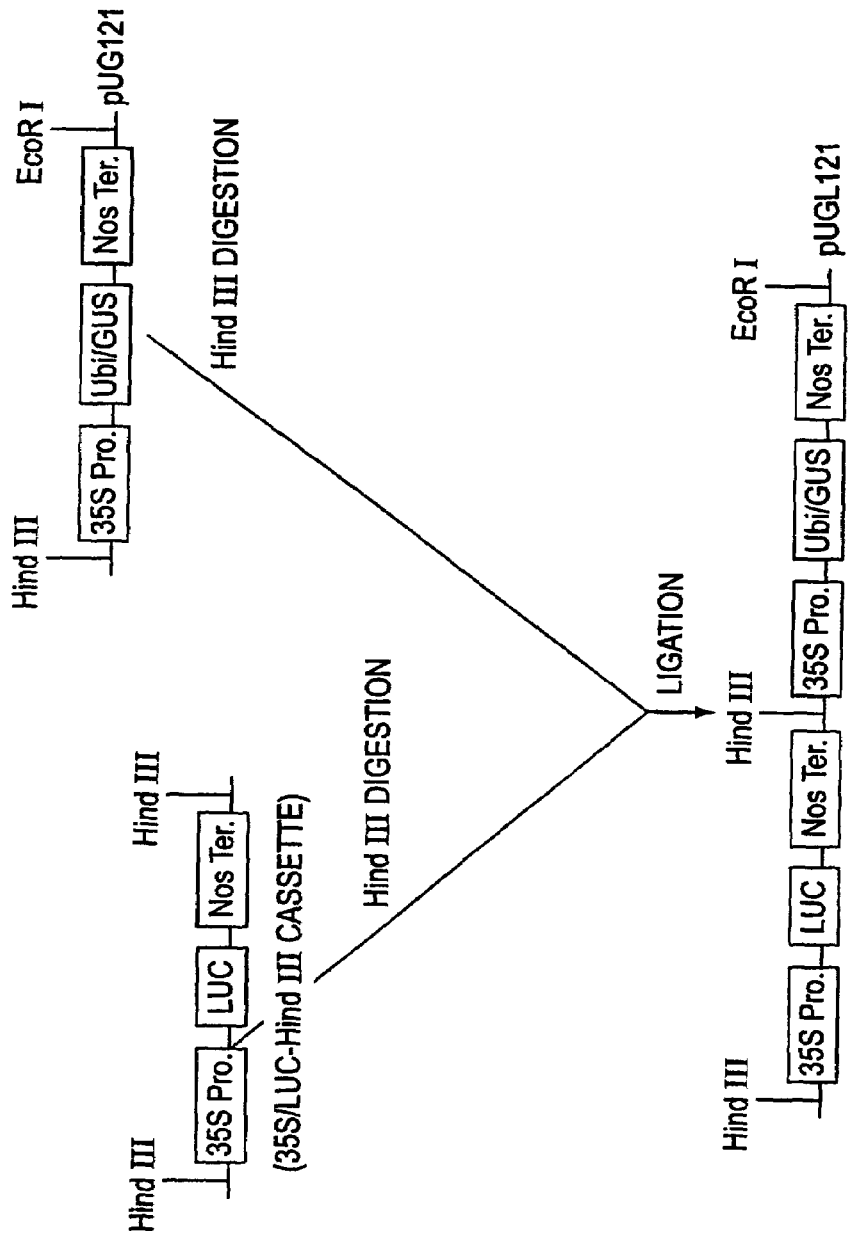
FIG. 7 illustrates the construction of ubiquitin-GUS fusion/LUC dual report binary vector pUGL121.
Figure 8:
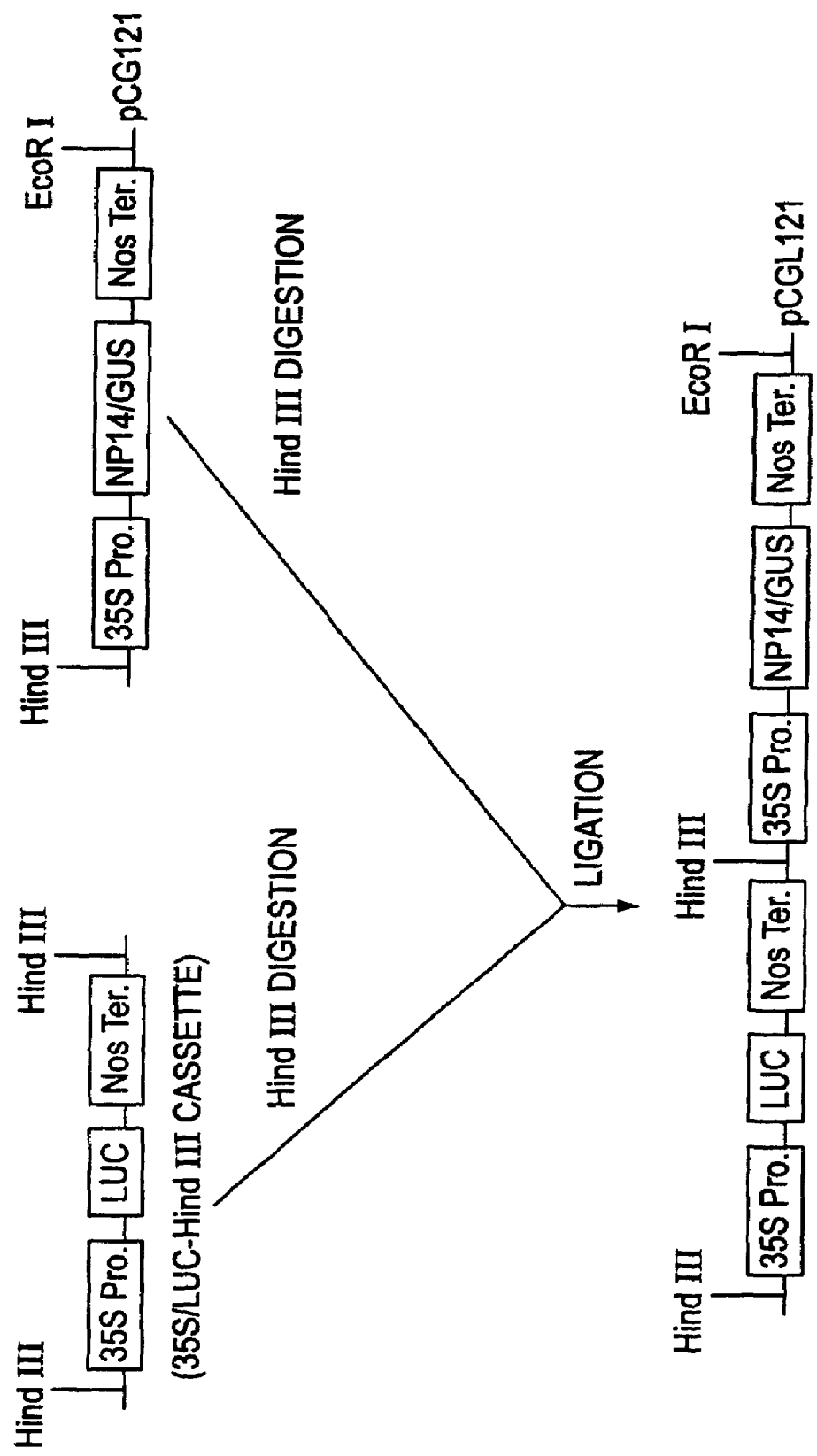
FIG. 8 illustrates the construction of the NP14-GUS fusion/LUC dual reporter binary vector pCGL121.
Figure 9:
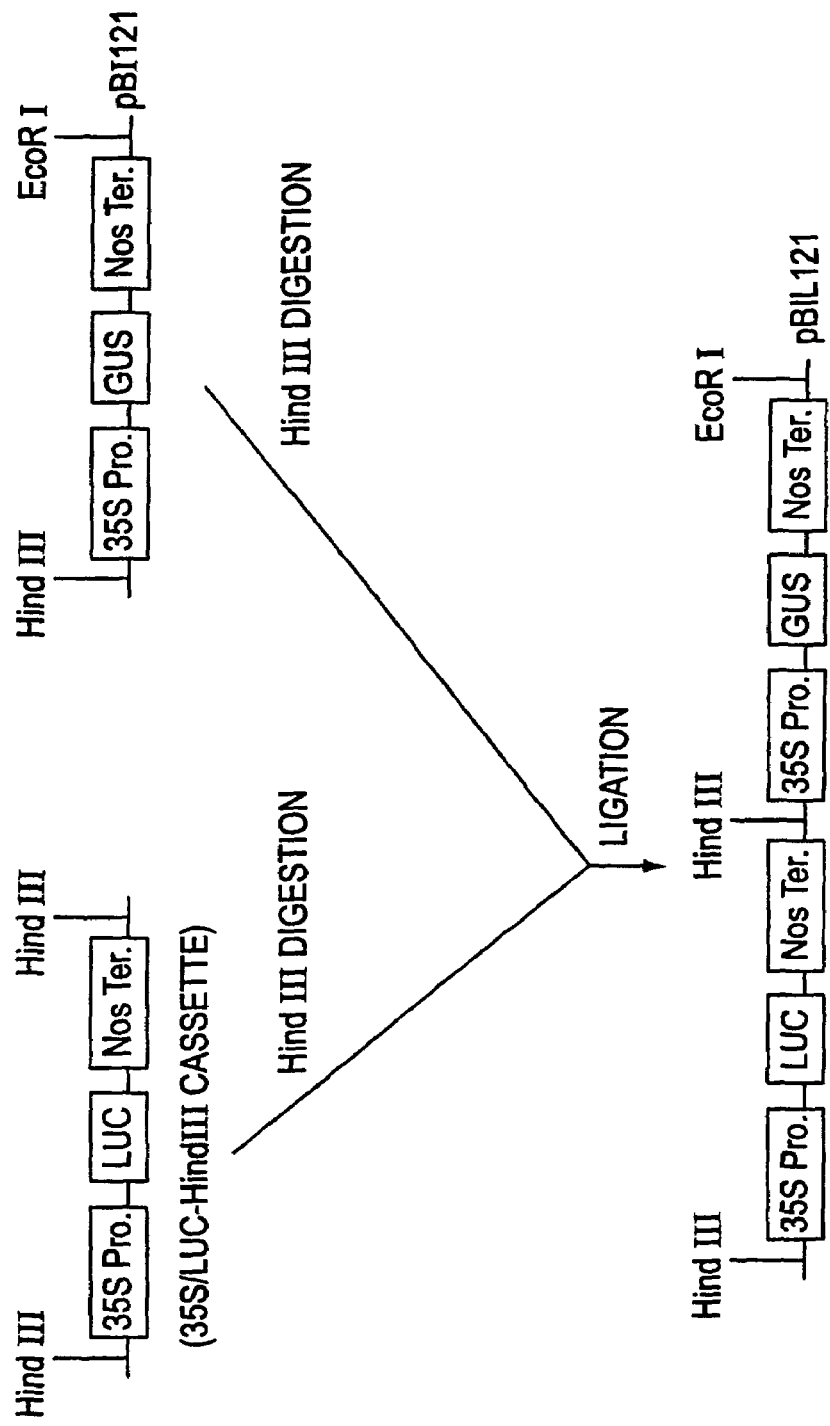
FIG. 9 illustrates the construction of the GUS/LUC dual reporter binary vector pBIL121.

To examine the enhancing effects of the N-terminal addition of the ubiquitin or CMV CP NP14 on GUS expression in stably transformed plants, a series of GUS/LUC (test/reference) dual reporter constructs were made. Essentially they are based on the fusion constructs used in transient expression assays, namely, pUG and pCG. The chimeric GUS expression cassettes were moved into the plant transformation intermediate plasmid pBI121, resulting in pUG121 and pCG121, respectively. The expression cassette of the reference reporter LUC, which was constructed by replacing the GUS gene in pBI221 with the LUC gene, was pre-made as a HindIII fragment (HindIII-35S/LUC/NOS-HindIII) and then inserted into the unique HindIII site of pUG121, pCG121 and pBI121, respectively. The resulting GUS/LUC dual reporter constructs, pUGL121, pCGL121 and pBIL121 are shown in FIGS. 7, 8 and 9, respectively.

EXAMPLE 4

Ubiquitin Fusion Enhances the Expression of GUS and LUC in Tobacco Protoplasts

The ubiquitin-GUS fusion construct pUG or the control plasmid pBI221 was introduced into tobacco protoplasts derived from tobacco BY-2 suspension cells, together with a reference plasmid FFO which contained LUC gene driven by the 35S promoter. GUS activities were determined and normalized by luciferase activities. In four independent transfection experiments, the normalized GUS activities (Δ GUS) from pUG were considerably higher than those from pBI221. The averaged increase fold due to the ubiquitin fusion is 6.0 (Table 2). When using LUC as a reporter and GUS as an internal standard as expressed from pBI221, the normalized LUC activities from pUL were 1.37 to 3.11 fold higher than those from the control plasmid p35SLUC (35S-LUC-NOS) in three independent transfection experiments, with the average increase fold about 2 (Table 3).

EXAMPLE 5

CMV CP NP14 is a More Efficient Fusion Partner than Ubiquitin

The enhancing effects of the NP14 fusion on GUS and LUC expression in tobacco protoplasts were examined in experiments parallel to the above mentioned ubiquitin fusion study. The NP14-GUS fusion construct pCG produced an average 11-fold higher GUS activity than did pBI221. These results are shown in Table 2. Fusion of NP14 to LUC increased the LUC activity by 2.87 times, calculated by comparing the normalized LUC activity of pCL to that of p35SLUC. These results are shown in Table 3. It is apparent that NP14 is a more efficient fusion partner than ubiquitin in augmenting GUS and LUC expression in tobacco cells.

TABLE 2

Normalized GUS activities and enhancing fold of the N-terminal fusion constructs

| plasmid | pBI221 | pUG | | pCG | |
|---|---|---|---|---|---|
| activities | GUS | Δ GUS | E | Δ GUS | E |
| 1 | 293.3 | 3760.0 | 12.8 | 5743.0 | 19.6 |
| 2 | 206.7 | 584.3 | 2.8 | 940.8 | 4.6 |
| 3 | 856.7 | 3733.8 | 4.4 | 6708.0 | 7.8 |
| 4 | 100.0 | 408.8 | 4.1 | 1247.0 | 12.5 |
| average E value | | | 6.0 ± 2.2 | | 11.1 ± 3.2 |

Notes: 1. The normalized GUS activity ΔGUS is calculated by the formula $$\Delta GUS_n = \frac{GUS_n \times LUC_{221}}{LUC_n}$$

where n represents a particular GUS fusion construct, 221 represents pBI221.

2. The enhancing fold E is calculated as $$\frac{\Delta GUS_n}{GUS_{221}}$$

TABLE 3

Normalized LUC activities and enhancing fold of the N-terminal fusion constructs

| | p35S LUC | | pUL | | | pCL | | |
|---|---|---|---|---|---|---|---|---|
| Plasmid activities | ΔLUC | average ΔLUC | ΔLUC | average ΔLUC | E | ΔLUC | average ΔLUC | E |
| 1  1 | 252 | 290 | 274 | 396 | 1.37 | 457 | 491 | 1.70 |
|    2 | 329 | | 518 | | | 529 | | |
| 2  1 | 169 | 169 | 556 | 526 | 3.11 | 701 | 794 | 4.70 |
|    2 | ND | | 496 | | | 886 | | |
| 3  1 | 64 | 112 | 141 | 164 | 1.46 | 270 | 246 | 2.20 |
|    2 | 160 | | 181 | | | 254 | | |
|    3 | ND | | 170 | | | 214 | | |
| Mean ± SE | | | | 1.98 ± 0.56 | | | 2.87 ± 0.92 | |

Notes: 1. The normalized LUC activity ΔLUC is calculated by the formula $$\Delta LUC_n = \frac{LUC_n \times GUSp35SLUC}{GUS_n}$$

where n represents a particular LUC fusion construct.

2. The enhancing fold E is calculated as $$\frac{\Delta LUC_n}{LUCp35SLUC}.$$

EXAMPLE 6

Ubiquitin- and NP14-Fusion Enhance GUS Expression in Transgenic Plants

To examine the enhancing effects of the ubiquitin fusion and the NP14 fusion on GUS expression in stably transformed plants, three GUS/LUC (test/reference) dual reporter constructs were made based on the binary vector pBI121. pUGL121, pCGL121 and pBIL121 contained expression cassettes ubiquitin-GUS, NP14-GUS and GUS only (control), respectively, and the reference LUC expression cassette was integrated in each plasmid (FIGS. 7–9). Tobacco plants transformed with each of the three constructs were prepared and analyzed for GUS and LUC activities. Each plant was analyzed twice in two independent experiments and only those plants displaying reasonable consistency of the relative GUS activities (GUS/LUC) in two experiments % were included for comparison. As shown in Table 4, although variations in the relative GUS activities existed among different transformants from the same constructs, the average GUS expression level of 5 qualified plants containing the 35S-ubiquitin/GUS fusion construct was 4 times higher than that derived from 6 plants containing the 35S-GUS construct, confirming the enhancing effect of the ubiquitin fusion on GUS expression as previously observed in tobacco protoplasts. Again, the NP14 fusion displayed a higher enhancing effect on GUS expression than did the ubiquitin fusion. The average relative GUS activity of 14 pCGL plants was about 7 fold that derived from the pBIL121 construct.

EXAMPLE 7

Ubiquitin Fusion and NP14 Fusion Cloning Vectors pBIubi (FIG. 10) and pBINP14 (FIG. 11) are two fusion protein expression vectors allowing for insertion of target genes downstream of the ubi.NC89 and the CMV CP NP14 coding sequence, respectively. Both vectors are derivatives of pBI221, with the GUS gene being replaced by the ubi.NC89 or NP14 coding sequence. In pBIubi, a polylinker sequence was attached to the 3' end of the ubi.NC89 sequence and the penultimate codon of the ubi.NC89 was changed from GGT to GGA for creating a StuI site in the polylinker region. In pBINP14, two cloning sites SalI (here equivalent to an AccI site) and SstI, are available for cloning the target genes downstream from the NP14 sequence (the last 5 base pairs of the NP14 sequence form part of the SalI recognition sequence). In order to use AccI instead of SalI for cleaving pBINP14, the AccI site at −393 of the CaMV 35S promoter was eliminated.

TABLE 4

Effects of ubiquitin- and NP14-fusion on GUS expression in trangenic tobacco plants Relative GUS activities: GUS/LUC (pmol MU min$^{-1}$/cpm × 10$^{-3}$)

| Plant lines | pUGL121 | | | pCGL121 | | | pBIL121 | | |
|---|---|---|---|---|---|---|---|---|---|
| | exp. 1 | exp. 2 | average | exp. 1 | exp. 2 | average | exp. 1 | exp. 2 | average |
| 1 | 12.9 | 15.3 | 14.1 | 2.4 | 3.4 | 2.9 | 1.4 | 2.6 | 2 |
| 2 | 13 | 43 | 28 | 4.5 | 6.8 | 5.65 | 5.2 | 2.4 | 3.8 |
| 3 | 0.7 | 0.5 | 0.6 | 63.2 | 9.5 | 36.35 | 4.2 | 0.6 | 2.4 |
| 4 | 0.3 | 0.4 | 0.35 | 26.9 | 8.3 | 17.6 | 2.5 | 5.4 | 3.95 |
| 5 | 4.8 | 0.8 | 2.8 | 17.8 | 22.2 | 20 | 0.4 | 0.38 | 0.39 |
| 6 | | | | 2.1 | 5 | 3.55 | 0.5 | 0.82 | 0.66 |
| 7 | | | | 4.6 | 5.8 | 5.2 | | | |
| 8 | | | | 58.7 | 20.2 | 39.45 | | | |
| 9 | | | | 15.6 | 3.6 | 9.6 | | | |
| 10 | | | | 17.2 | 4.4 | 10.8 | | | |
| 11 | | | | 3 | 1.4 | 2.2 | | | |
| 12 | | | | 17.9 | 24.2 | 21.05 | | | |
| 13 | | | | 20.7 | 19.4 | 20.05 | | | |
| 14 | | | | 13.7 | 25.3 | 19.5 | | | |
| Mean ± SE | | 9.17 ± 5.34 | | | 15.28 ± 3.18 | | | 2.2 ± 0.61 | |

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for enhancing production of a desired protein as part of a fusion protein in a plant cell or a plant which method comprises providing a nucleic acid which encodes a fusion protein to a plant cell or plant, wherein the fusion protein comprises the protein of SEQ ID NO: 4 linked to the desired protein and wherein the desired protein is heterologous to the protein of SEQ ID NO:4.

2. The method of claim 1 wherein the carboxy terminus of said protein of SEQ ID NO:4 forms a peptide linkage with the amino terminus of said desired protein.

3. The method of claim 1 wherein said nucleic acid comprises nucleotides 6–47 of SEQ ID NO:3.

4. The method of claim 1 wherein said nucleic acid is under the control of a CaMV 35S promoter.

5. A nucleic acid vector comprising a plant-expressible promoter operably linked to a nucleic acid which encodes a fusion protein wherein said fusion protein comprises the protein of SEQ ID NO:4 linked to a protein of interest, wherein the protein of interest is heterologous to the protein of SEQ ID NO:4.

6. The vector of claim 5 wherein said protein of SEQ ID NO:4 is linked in a peptide linkage at its carboxy terminus to the amino terminus of said protein of interest.

7. The vector of claim 5 wherein said nucleic acid is under the control of a CaMV 35S promoter.

8. The vector of claim 5 wherein said vector comprises nucleotides 6–47 of SEQ ID NO:3.

9. A plant cell or a plant comprising the vector of claim 5.

10. An isolated nucleic acid comprising SEQ ID NO:3.

11. An isolated nucleic acid consisting of SEQ ID NO:3.

12. The method of claim 1, wherein the plant cell or plant is transfected with the nucleic acid.

13. The method of claim 1, wherein the plant cell or plant is transformed with the nucleic acid.

14. A plant cell or a plant comprising the vector of claim 6.

15. A plant cell or a plant comprising the vector of claim 7.

* * * * *

SEQUENCE LISTING

<160> NUMBER OF SEQ ID NOS: 14

<210> SEQ ID NO 1
<211> LENGTH: 235
<212> TYPE: DNA
<213> ORGANISM: Nicotiana tabacum
<220> FEATURE:
<221> NAME/KEY: CDS
<222> LOCATION: (3)..(230)
<223> OTHER INFORMATION: Modified from wild-type to insert an SphI site
      in the region encompassing the initiation codon ATG
      and to insert an NcoI site following the last
      codon GGC.

<400> SEQUENCE: 1

```
gc atg cag atc ttc gta aag acc ctg acg ggg aag act att acc tta        47
   Met Gln Ile Phe Val Lys Thr Leu Thr Gly Lys Thr Ile Thr Leu
   1               5                  10                  15 gag gta gag tca tcg gac acc att gac aat gtt aag gct aag att cag       95
Glu Val Glu Ser Ser Asp Thr Ile Asp Asn Val Lys Ala Lys Ile Gln
             20                  25                  30 gac aag gaa ggc att cca ccg gac cag cag cgg ttg att ttc gca ggt      143
Asp Lys Glu Gly Ile Pro Pro Asp Gln Gln Arg Leu Ile Phe Ala Gly
         35                  40                  45 aag cag ctt gag gat ggc cga aca cta gct gac tac aac atc cag aag      191
Lys Gln Leu Glu Asp Gly Arg Thr Leu Ala Asp Tyr Asn Ile Gln Lys
     50                  55                  60 gag tcc act ctc cat ctc gtc tta aga ctc cgc ggt ggc catgg            235
Glu Ser Thr Leu His Leu Val Leu Arg Leu Arg Gly Gly
 65                  70                  75
```

```
<210> SEQ ID NO 2
<211> LENGTH: 76
<212> TYPE: PRT
<213> ORGANISM: Nicotiana tabacum

<400> SEQUENCE: 2

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly
65                  70                  75

<210> SEQ ID NO 3
<211> LENGTH: 53
<212> TYPE: DNA
<213> ORGANISM: cucumber mosaic virus
<220> FEATURE:
<221> NAME/KEY: CDS
<222> LOCATION: (6)..(47)

<400> SEQUENCE: 3 gatcc atg gac aaa tct gaa tca acc agt gct ggt cgt aac cgt cga         47
      Met Asp Lys Ser Glu Ser Thr Ser Ala Gly Arg Asn Arg Arg
       1               5                  10 cgagct                                                                53

<210> SEQ ID NO 4
<211> LENGTH: 14
<212> TYPE: PRT
<213> ORGANISM: cucumber mosaic virus

<400> SEQUENCE: 4

Met Asp Lys Ser Glu Ser Thr Ser Ala Gly Arg Asn Arg Arg
 1               5                  10

<210> SEQ ID NO 5
<211> LENGTH: 13
<212> TYPE: DNA
<213> ORGANISM: Plasmid pSKUBC1
<220> FEATURE:
<221> NAME/KEY: misc_feature
<222> LOCATION: ()..()
<223> OTHER INFORMATION: Joining region of fusion of two genes.

<400> SEQUENCE: 5
ggccatggac aaa                                                        13

<210> SEQ ID NO 6
<211> LENGTH: 33
<212> TYPE: DNA
<213> ORGANISM: Plasmid pBI221
<220> FEATURE:
<221> NAME/KEY: misc_feature
<222> LOCATION: (1)..(33)
<223> OTHER INFORMATION: Joining region between 35S promoter and GUS
      gene.

<400> SEQUENCE: 6
tctagaggat ccccgggtgg tcagtccctt atg                                  33
```

```
<210> SEQ ID NO 7
<211> LENGTH: 18
<212> TYPE: DNA
<213> ORGANISM: Plasmid pUG
<220> FEATURE:
<221> NAME/KEY: misc_feature
<222> LOCATION: (1)..(18)
<223> OTHER INFORMATION: Joining region of fusion of genes.

<400> SEQUENCE: 7
ggccatggat ccccgggt                                                   18

<210> SEQ ID NO 8
<211> LENGTH: 18
<212> TYPE: DNA
<213> ORGANISM: Plasmid pUCG2
<220> FEATURE:
<221> NAME/KEY: misc_feature
<222> LOCATION: (1)..(18)
<223> OTHER INFORMATION: Joining region of fusion of genes.

<400> SEQUENCE: 8
ctccgcggtg gcatggac                                                   18

<210> SEQ ID NO 9
<211> LENGTH: 29
<212> TYPE: DNA
<213> ORGANISM: Plasmid pBIubi
<220> FEATURE:
<221> NAME/KEY: misc_feature
<222> LOCATION: (1)..(29)
<223> OTHER INFORMATION: Joining region between promoter and fused gene.

<400> SEQUENCE: 9
tctagaacta gtggatccct ggcatgcag                                       29

<210> SEQ ID NO 10
<211> LENGTH: 35
<212> TYPE: DNA
<213> ORGANISM: Plasmid pBIubi
<220> FEATURE:
<221> NAME/KEY: misc_feature
<222> LOCATION: (1)..(35)
<223> OTHER INFORMATION: Final 2 codons of the ubiquitin gene followed
      by polylinker sequence.

<400> SEQUENCE: 10
ggaggcctgt cgactcgagc ccgggtaccg agctc                                35

<210> SEQ ID NO 11
<211> LENGTH: 12
<212> TYPE: DNA
<213> ORGANISM: Plasmid pUL
<220> FEATURE:
<221> NAME/KEY: misc_feature
<222> LOCATION: (1)..(12)
<223> OTHER INFORMATION: Joining region between fusion of genes.

<400> SEQUENCE: 11
ggaggcatgg aa                                                         12

<210> SEQ ID NO 12
<211> LENGTH: 12
<212> TYPE: DNA
<213> ORGANISM: Plasmid pCL
<220> FEATURE:
<221> NAME/KEY: misc_feature
<222> LOCATION: (1)..(12)
```

```
-continued

<223> OTHER INFORMATION: Joining region between fusion of genes.

<400> SEQUENCE: 12
cgtcgcatgg aa                                                          12

<210> SEQ ID NO 13
<211> LENGTH: 29
<212> TYPE: DNA
<213> ORGANISM: Plasmid pBIubi
<220> FEATURE:
<221> NAME/KEY: misc_feature
<222> LOCATION: (1)..(29)
<223> OTHER INFORMATION: Joining region of fusion of promoter and gene.

<400> SEQUENCE: 13
tctagaacta gtggatccct ggcatgcag                                        29

<210> SEQ ID NO 14
<211> LENGTH: 35
<212> TYPE: DNA
<213> ORGANISM: Plasmid pBIubi
<220> FEATURE:
<221> NAME/KEY: misc_feature
<222> LOCATION: (1)..(35)
<223> OTHER INFORMATION: Joining region with multicloning sequence
      between fusion of gene and terminator.

<400> SEQUENCE: 14
ggaggcctgt cgactcgagc ccgggtaccg agctc                                 35
```